United States Patent [19]

Wöldike

[11] Patent Number: 5,252,726
[45] Date of Patent: Oct. 12, 1993

[54] PROMOTERS FOR USE IN ASPERGILLUS

[75] Inventor: Helle F. Wöldike, Lynge, Denmark

[73] Assignee: Novo Nordisk A/S, Bagsvaerd, Denmark

[21] Appl. No.: 859,596

[22] Filed: Mar. 23, 1992

Related U.S. Application Data

[63] Continuation of Ser. No. 469,509, Mar. 13, 1990, abandoned.

[30] Foreign Application Priority Data

Sep. 4, 1987 [DK] Denmark .............................. 4609/87
Sep. 29, 1987 [DK] Denmark .............................. 5126/87

[51] Int. Cl.$^5$ ...................... C12N 15/56; C12N 15/11
[52] U.S. Cl. .................................. 536/24.1; 435/203
[58] Field of Search .............. 536/27; 435/69.1, 172.3, 435/203, 254, 201

[56] References Cited

FOREIGN PATENT DOCUMENTS 8606097 10/1986 PCT Int'l Appl. .

OTHER PUBLICATIONS

Nakajima et al. (1986), Appl. Microbiol. Biotechnol., vol. 23, pp. 355-360.

*Primary Examiner*—Richard A. Schwartz
*Assistant Examiner*—Philip W. Carter
*Attorney, Agent, or Firm*—Steve T. Zelson; Cheryl H. Agris

[57] ABSTRACT

A process for expression of a protein product in Aspergillus is disclosed. The process comprises transforming an Aspergillus strain with a vector system comprising DNA-sequences encoding a promoter including upstream activating sequences derived from an *A. niger* amylase, a suitable marker for selection of transformants, and a DNA-sequence encoding the desired protein product. The process enables industrial production of many different polypeptides and proteins in Aspergillus, preferably *A. niger*. Examples of such products are chymosin or prochymosin and other rennets, proteases, lipases and amylases. Also disclosed is an effective promoter for expression of a protein in Aspergillus, preferably Aspergillus niger being derived from a gene encoding an *A. niger* amylase. The *A. niger* amylases are the neutral and acid stable α-amylases and a new amylase not so far described and designated XA amylase. Also disclosed is the novel amylase from *A. niger* XA amylase.

2 Claims, 11 Drawing Sheets

FIG. 1
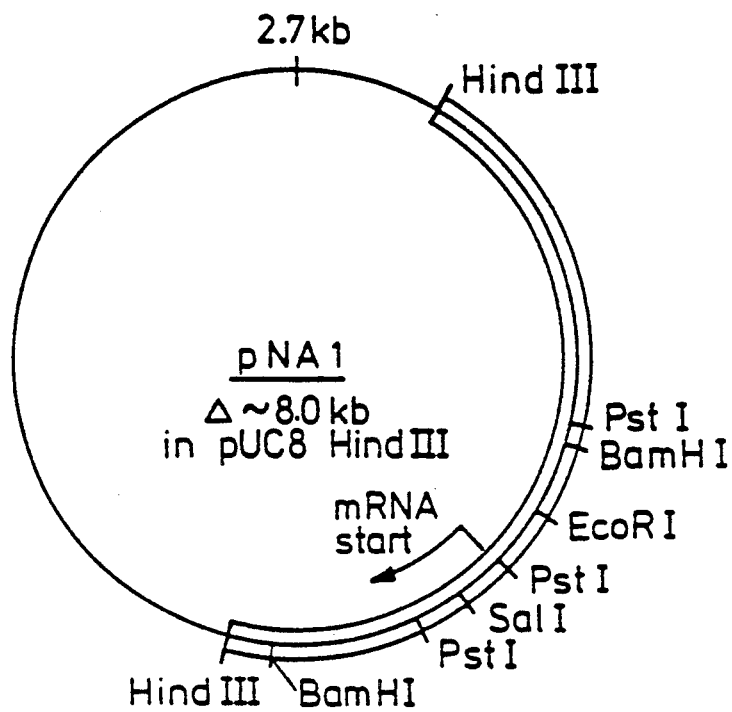
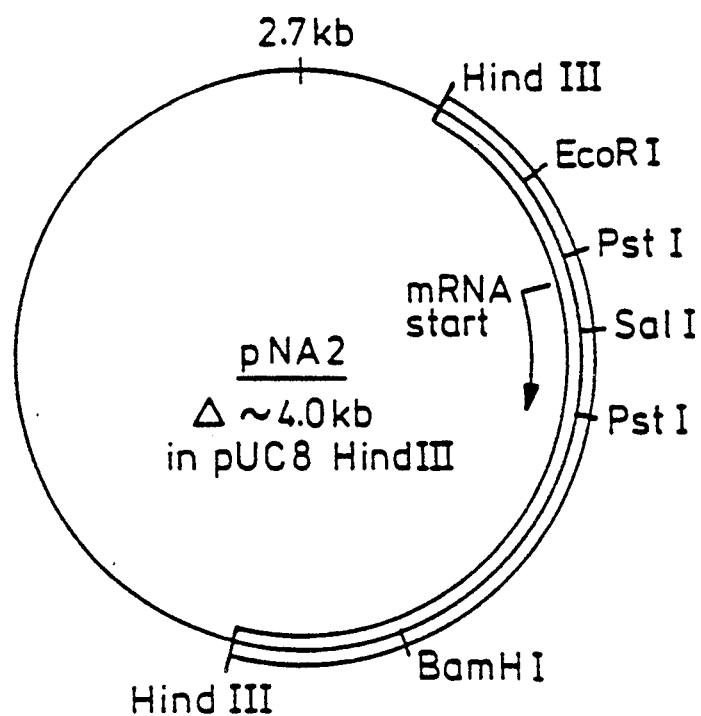

FIG. 2

```
-1456 TCTAAACGTC GTCAAAGGTC TGTCTTCTTT CCGTATTGTC ATCTTGTAAT
-1406 ACGCTTCCTC AATGTCGTAT TTCGAAAAGA AACGGGCTTT CTTTATCCAA
-1356 TCCCTGTGGT AAGATTGATC GTCAGGAGAT TATCTGCAGG AAACATCATG
-1306 GTGGGTAAC CAAGGTTGTG TCTGTATAAT ATATACATGT AAAATACATG
-1256 AGCTTCGGTG ATATAATACA GAAGTACCAT ACAGTACCGC GTTATGAAAA
-1206 CACATTAATC CGGATCCTTT CCTATAATAG ACTAGCGTGC TTGGCATTAG
-1156 GGTTCGAAAA ACAATCGAAG AGTATAAGGG GATGACAGCA GTAACGACTC
-1106 CAACTGTACG CCTCCGGGTA GTAGTCCGAG CAGCCGAGCC AGCTCAGCGC
-1056 CTAAAACGCC TTATACAATT AAGCAGTTAA AGAAGTTAGA ATCTACGCTT
-1006 AAAAAGCTAC TTAAAAATCG ATCTCGCAGT CCCGATTCGC CTATCAAAAC
 -956 CAGTTTAAAT CAACTGATTA AAGGTGCCGA ACGAGCTATA AATGATATAA
 -906 CAATATTAAA GCATTAATTA GAGCAATATC AGGCCGCGCA CGAAAGGCAA
 -856 CTTAAAAGCG AAAGCGCTCT ACTAAACAGA TTACTTTTGA AAAAGGCACA
 -806 TCAGTATTTA AAGCCCGAAT CCTTATTAAG CGCCGAAATC AGGCAGATAA
 -756 AGCCATACAG GCAGATAGAC CTCTACCTAT TAAATCGGCT TCTAGGCGCG
 -706 CTCCATCTAA ATGTTCTGGC TGTGGTGTAC AGGGGCATAA AATTACGCAC
 -656 TACCCGAATC GATAGAACTA CTCATTTTTA TATAGAAGTC AGAATTCATG
 -606 GTGTTTTGAT CATTTTAAAT TTTTATATGG CGGGTGGTGG GCAACTCGCT
 -556 TGCGCGGCAA CTCGCTTACC GATTACGTTA GGGCTGATAT TTACGTAAAA
 -506 ATCGTCAAGG GATGCAAGAC CAAAGTAGTA AAACCCCGGA GTCAACAGCA
 -456 TCCAAGCCCA AGTCCTTCAC GGAGAAACCC CAGCGTCCAC ATCACGAGCG
 -406 AAGGACCACC TCTAGGCATC GGACGCACCA TCCAATTAGA AGCAGCAAAG
 -356 CGAAACAGCC CAAGAAAAAG GTCGGCCCGT CGGCCTTTTC TGCAACGCTG
 -306 ATCACGGGCA GCGATCCAAC CAACACCCTC CAGAGTGACT AGGGGCGGAA
 -256 ATTTAAAGGG ATTAATTTCC ACTCAACCAC AAATCACAGT CGTCCCCGGT
 -206 ATTGTCCTGC AGAATGCAAT TTAAACTCTT CTGCGAATCG CTTGGATTCC
 -156 CCGCCCCTAG CGTAGAGCTT AAAGTATGTC CCTTGTCGAT GCGATGTATC
 -106 ACAACATATA AATACTAGCA AGGGATGCCA TGCTTGGAGG ATAGCAACCG
  -56 ACAACATCAC ATCAAGCTCT CCCTTCTCTG AACAATAAAC CCCACAGAAG
   -6 GCATTT
```

1
ATGATGGTCGCGTGGTGGTCTCTATTTCTGTACGGCCTTCAGGTCGCGGCACCT
MetMetValAlaTrpTrpSerLeuPheLeuTyrGlyLeuGlnValAlaAlaPro

64
GCTTTGGCTGCAACGCCTGCGGACTGGCGATCGCAATCCATTTATTTCCTTCTC
AlaLeuAlaAlaThrProAlaAspTrpArgSerGlnSerIleTyrPheLeuLeu
                 mature neutral α-amylase ACGGATCGATTTGCAAGGACGGATGGGTCGAC
ThrAspArgPheAlaArgThrAspGlySer

FIG. 3

```
-927 AAGCTTCCAG CTACCGTAGA TTACTGATAC AAACTCAATA CACTATTTCT
-877 ATAACCTTAC TGTTCAATAC AGTACGATCA AAATTTCCGG AATATTAATG
-827 TTACGGTTAC CTTCCATATG TAGACTAGCG CACTTGGCAT TAGGGTTCGA
-777 AATACGATCA AAGAGTATTG GGGGGGGTGA CAGCAGTAAT GACTCCAACT
-727 GTAAATCGGC TTCTAGGCGC GCTCCATCTA AATGTTCTGG CTGTGGTGTA
-677 CAGGGGCATA AAATTACGCA CTACCCGAAT CGATAGAACT ACTCATTTTT
-627 ATATAGAAGT CAGAATTCAT GGTGTTTTGA TCATTTTAAA TTTTTATATG
-577 GCGGGTGGTG GGCAACTCGC TTGCGCGGCA ACTCGCTTAC CGATTACGTT
-527 AGGGCTGATA TTTACGTAAA AATCGTCAAG GATGCAAGA CCAAAGTACT
-477 AAACCCCGG AGTCAACAGC ATCCAAGCCC AAGTCCTTCA CGGAGAAACC
-427 CCAGCGTCCA CATCACGAGC GAAGGACCAC CTCTAGGCAT CGGACGCACC
-377 ATCCAATTAG AAGCAGCAAA GCGAAACAGC CCAAGAAAAA GGTCGGCCCG
-327 TCGGCCTTTT CTGCAACGCT GATCACGGGC AGCGATCCAA CCAACACCCT
-277 CCAGAGTGAC TAGGGGCGGA AATTTATCGG GATTAATTTC ICACTCAACCA
-227 CAAATCACAG TCGTCCCCGG TATTGTCCTG CAGAATGCAA TTTAAACTCT
-177 TCTGCGAATC GCTTGGATTC CCCGCCCCTA GCGTAGAGCT TAAAGTATGT
-127 CCCTTGTCGA TGCGATGTAT CACAACATAT AAATACTAGC AAGGGATGCC
 -77 ATGCTTGGAG GATAGCAACC GACAACATCA CATCAAGCTC TCCCTTCTCT
 -27 GAACAATAAA CCCCACAGAA GGCATTT
```

```
   1
  ATGATGGTCGCGTGGTGGTCTCTATTTCTGTACGGCCTTCAGGTCGCGGCACCT
  MetMetValAlaTrpTrpSerLeuPheLeuTyrGlyLeuGlnValAlaAlaPro
              64
  GCTTTGGCTGCAACGCCTGCGGACTGGCGATCGCAATCCATTTATTTCCTTCTC
  AlaLeuAlaAlaThrProAlaAspTrpArgSerGlnSerIleTyrPheLeuLeu
             mature neutral α-amylase →

ACGGATCGATTTGCAAGGACGGATGGGTCGAC
  ThrAspArgPheAlaArgThrAspGlySer
```

FIG. 5

```
-1276 CCTAATGACC CAACATTGGC TGCGGTTGAG ACTCAATTCA TGGTTGGGCC
-1226 GGCCATCATG GTGGTCCCGG TATTGGAGCC TCTGGTCAAT ACGGTCAAGG
-1176 GCGTATTCCC AGGAGTTGGA CATGGCGAAG TGTGGTACGA TTGGTACACC
-1126 CAGGCTGCAG TTGATGCGAA GCCCGGGGTC AACACGACCA TTTCGGCACC
-1076 ATTGGGCCAC ATCCCAGTTT ATGTACGAGG TGGAAACATC TTGCCGATGC
-1026 AAGAGCCGGC ATTGACCACT CGTGAAGCCC GGCAAACCCC GTGGGCTTTG
 -976 CTAGCTGCAC TAGGAAGCAA TGGAACCGCG TCGGGCAGC  TCTATCTCGA
 -926 TGATGGAGAG AGCATCTACC CCAATGCCAC CCTCCATGTG GACTTCACGG
 -876 CATCGCGGTC AAGCCTGCGC TCGTCGGCTC AAGGAAGATG GAAAGAGAGG
 -826 AACCCGCTTG CTAATGTGAC GGTGCTCGGA GTGAACAAGG TGCCCTCTGC
 -776 GGTGACCCTG AATGGACAGG CCGTATTTCC CGGGTCTGTC ACGTACAATT
 -726 CTACGTCCCA GGTTCTCTTT GTTGGGGGGC TGCAAAACTT GACGAAGGGC
 -676 GGCGCATGGG CGGAAAACTG GTATTGGAA  TGGTAGTGTC AGCCACAAGC
 -626 CAGGTGTGCG CGTACAGCAT GCAACATGGG AACGATGCTC TGCAATGTAG
 -576 CTCTTTGGTT ATAATTCAAA ATTCAACTTC CACCTTTGTT TCACCGGCGG
 -526 CCACGGCATT CCTGCATGAC TAACGTTCTG TAAATGGACC CGATAACACC
 -476 CAGCACGTTG CAGCAGAGAA GGTACTCTCT CACACGCACT GCTCTTTATA
 -426 GTTGCCGAGA CGGCCGCCGA GGAGAAAACC GCCGGCCTGT GGCCACTATT
 -376 CGCTGGAAGG AACCCTGCCA GTCAACACA  CCCGCCCGTG ATCGCCAGGG
 -326 GCCGATGGAT TTCCCCCCGC ATCCTTGTCG GTTCATGAGT GAAGACTTTA
 -276 AATCCCATCT AGCTGACGGT CGGGTACATC AATAACTGGC GGCCTGGTTT
 -226 CCAGGACACG GAGAGGCATC TAATCGCTAT TTATAGAATG CTGGGATCGG
 -176 ACCCGTCGAA TGGTCTTCCG ATGGGAAGTG ACAACTCACA TTGTCATGTT
 -126 GGCCTTACTC AATCCAACGG GATCTGACCT GCTTTGGCTA ACCTAGTATA
  -76 AATCAGCATG TCTCTCCTTT GATACATCGG ATCGTTCCTC AAATATAGTT
  -26 ATATCTTCGA AAAATTGACA AGAAGG
```

```
   1
ATGACAATCTTTCTGTTTCTGGCCATTTTCGTGGCTACAGCTCTGGCAGCCACG
MetThrIlePheLeuPheLeuAlaIlePheValAlaThrAlaLeuAlaAlaThr
signal                                          mature CCTGCAGAATGGCGCTCCCAGTCGATATATTTCCTGCTCACCGATCGCTTTGCG
ProAlaGluTrpArgSerGlnSerIleTyrPheLeuLeuThrAspArgPheAla
   amylase CGAACGGATAATTCTACCACTGCTTCTTGTGACTTGAGCGCTCGGGTTAGTCAC
ArgThrAspAsnSerThrThrAlaSerCysAspLeuSerAlaArg intron
```

FIG. 7A

```
         10         20         30         40         50         60
 CTTAATCACG GGAGCCTTTA TCCGTCGCAC CGGCCAATTT AAGGTCCTCT TGATCCTTGC
         70         80         90        100        110        120
 CGGTCTCGTT GCGTCCGTCG CCTATCTACT CCTCATCCTT CGCTGGAACG GTCATACTGG
        130        140        150        160        170        180
 ATTCTGGGAG TCCTTGTATA TTATTCCCGG TGGTATGGGT ACTGGTTTCT GCTCTGCAGC
        190        200        210        220        230        240
 TGCTTTTGTC AGTATGACGG CGTTTTTGAT GCCGCAGGAA GTGGCCATGG CAACAGGAGG
        250        260        270        280        290        300
 TTACTTCCTA TTATTCAGCT TCGCATGACG GCCGGTGTGA CTGTCACTAA CAGTCTGCTG
        310        320        330        340        350        360
 GGGACGGTTT TCAAGCGCCA GATGGAACAG CACCTGACGG GTCCAGGAGC CAAGAAGGTT
        370        380        390        400        410        420
 GGTATCCCCG CACCTTTGCT GCGTCACTTA CTAACAGATT TTTTGAAGAT CATCGAGCGC
        430        440        450        460        470        480
 GCGCTATCCG ACACGAGCTA TATCAACGGT TTGCAGGGTC ATGTCCGGGA TGTAGTGGTA
        490        500        510        520        530        540
 CAAGGATATG TGACTGGTCT CCGCTACACT TACTGTAAGT CGTTTGGATC ATGCATCCAC
        550        560        570        580        590        600
 CATCCACCTT ATTAACTTGG TGCCAGTGTT TTCCCTCATT CTTTCGCTTC TTGGATCGGT
        610        620        630        640        650        660
 CCTCGCTTGG ACTGTACGAA AACACCAACT ATGAGGAACC AGTACGGCAG CTGATAGTAT
        670        680        690        700        710        720
 CCGAAAGCTG CAAATTGCTT CATCGAGGCT GGCATTCGAT AGAAGAAAGA ATTATAGACA
        730        740        750        760        770        780
 ACTAGTCTTG CAATATGACA ATTCTCTTTG ATTAATAAAT GAAAGCACGC ATGTATCAGC
        790        800        810        820        830        840
 CTAATAGCCG AGTGGCGGGC ATCTCTGGCG GCCTCCCGAG CAGCGTGGAA TGCGTCCAAG
        850        860        870        880        890        900
 ATCCCGTCCG CGGGTCGTCC TTCGGTCGGA ATGATGACTG GAGCAGCAGA CGATGTCCTG
        910        920        930        940        950        960
 AGCTGAATGC ATGTGATATT CACATTCCAG GGAGAATTGT CGGCTATTTA GAACCCTCTC
        970        980        990       1000       1010       1020
 GGCTTAAAAG CCCTATTAGA CTATGGGTGC GCTCAAGCCA CTAGCCAGGA TATCCCGCTG
       1030       1040       1050       1060       1070       1080
 AACGCTCCAT CACCTTGCAG CTGAAGTGCA ACATGGGACG GGCTTTAACT TTTCGTAGAT
       1090       1100       1110       1120       1130       1140
 ATAAGTTTAA TTTATCCTCT CCACACCCAT AGGGTCGTAT GGTGTCAACC GGTGTAGTCT
       1150       1160       1170       1180       1190       1200
 GCAGGATTTC ATCTCGCTTC GCCAAGCGAG GCGCCTAACG GGCAGCCTGC AGCTTACCCT
```

Fig. 7b

```
         1210       1220       1230       1240       1250       1260
     GTTAACCCCG GCTCACCACC CCCCGAGCAA TCCGTCGCGT CCTCCACGAG TCATAACAAG 1270       1280       1290       1300       1310       1320
     GTTCGGGCGT TGTTTCTTAC CCCCACTATC AGGCGTATTC AGTTAACAGT CAGTAGTCCC 1330       1340       1350       1360       1370       1380
     GTGTCGGAGA TTTGTTGTTC TGCAACAATT AAAGGGGACC AGGGTTAAAT CCTGGCCCCC 1390       1400       1410       1420       1430       1440
     GAACTGATCG GAGTTTCGGC CAATGAGAGA TGTTGTATAC CCCCGTTCCT GGCAGATGGA 1450       1460       1470       1480       1490       1500
     TTAATTGCCG GCTCCATTTG GCATCCATCA AGCATCATAC GGGATTAGAA GGGTAGTTCG 1510       1520       1530       1540       1550       1560
     TGGGTTGATC TGCCGTGCAA GGTGCTCAAG GCTCTGGAGT CATGCTGAAC GCAAATATTT 1570       1580       1590       1600       1610       1620
     AAGAATCGTC GTCAGGGACA GCGTTCTCTG GATAGTCAAG CTGTGCTTTG GGACGCTGTT 1630       1640       1650       1660       1670       1680
     CTGTCGCTTT GTCAAAACAT AATTCGCAGC GATGAGATTA TCGACTTCGA GTCTCTTCCT
                                      MetArgLeu  SerThrSer  SerLeuPheLeu
                                      signal 1690       1700       1710       1720       1730       1740
     TTCCGTGTCT CTGCTGGGGA AGCTGGCCCT CGGGCTGTCG GCTGCAGAAT GGCGCACTCA
     SerValSer  LeuLeuGly  LysLeuAla  LeuGlyLeuSer AlaAlaGlu  TrpArgThrGln
                                                  Mature acid-stable amylase ▸

1750       1760       1770       1780       1790       1800
     GTCGATTTAC TTCCTATTGA CGGATCGGTT CGGTAGGACG GACAATTCGA CGACAGCTAC
     SerIleTyr  PheLeuLeu  ThrAspArgPhe GlyArgThr  AspAsnSer  ThrThrAla
```

PROMOTERS FOR USE IN ASPERGILLUS

This application is a continuation of application of application Ser. No. 07/469,509, filed Mar. 13, 1990, now abandoned, which is a continuation of application Ser. No. PCT/DK88/00145, filed on Sep. 2, 1988, now abandoned.

BACKGROUND OF THE INVENTION

The present invention relates to a process for expression of protein products in Aspergillus, recombinant DNA vectors, a promoter for Aspergillus and transformed fungi. The present invention is also directed to a new amylase from *A. niger*.

In the past, numerous processes have been developed for the production of polypeptides or proteins by means of the recombinant DNA technology. The main interest has been concentrated on bacteria and yeast, e.g. *E. coli, Bacillus subtilis* and *Saccharomyces cerevisiae* being well characterized species as regards for instance expression and selection systems.

Besides the above mentioned microorganisms, filamentous fungi, such as *Aspergillus niger*, are attractive candidates as host microorganisms for recombinant DNA vectors being well-characterized and widely used microorganisms for the commercial production of enzymes. Efforts have especially been concentrated on the development of transformation systems by which a selection marker permitting selection of transformants from the untransformed host microorganisms is used.

In the last few years different selection markers for the transformation of *Aspergillus nidulans* have been described and procedures have been developed for integrative transformation of the filamentous fungus *Aspergillus nidulans* for the purpose of investigation of the genetic and molecular processes controlling fungal cell differentiation.

Transformation of *A. nidulans* has been demonstrated by using plasmids containing the *Neurospora crassa* pyr-4 gene (Ballance, D. J. et al., Biochem. Biophys. Res. Commun , 112 (1983) 284–289), the *A. nidulans* amdS gene (Tilburn, J. G. et al., Gene 26 (1983) 205–221), the *A. nidulans* trpC gene (Yelton, M. M. et al., Proc. Natl. Acad. Sci. U.S.A., 81 (1984) 1470–1474) and the *A. nidulans* argB gene (John, M. A. and Peberdy J., Microb. Technol. 6 (1984) 386–389). The transforming DNA was found to be integrated into the host genome at rather low frequencies (typically <1000 transformants/μg of DNA).

Recently transformation of *Aspergillus niger* with the amdS gene of *A. nidulans* was described (Kelly, J. M. and Hynes, M. J., EMBO Journal 4 (1985), 475–479) and amdS was shown to be a potential selection marker for use in transformation of Aspergillus niger that cannot grow strongly on acetamide as a sole nitrogen source. Transformation of *Aspergillus niger* using the argB gene of *Aspergillus nidulans* has also been described recently (Buxton, F. P. et al., Gene 37 (1985), 207–214).

So far yields of heterologous proteins have not been satisfactory in *A. niger* for commercial production. Accordingly, it is the object of the present invention to provide a method for obtaining commercially attractive yields of foreign proteins in Aspergillus. It is also an object of the present invention to enhance the production of homologous proteins in Aspergillus.

BRIEF DESCRIPTION OF THE INVENTION

According to the present invention it has now been shown that it is possible to obtain a high level of expression of heterologous proteins or to enhance the production of homologous proteins in Aspergillus when using promoters derived from amylase genes from *A. niger*.

As used herein the expression "heterologous proteins" means proteins not produced by the host organism whereas "homologous proteins" means proteins produced by the host organism.

According to a first aspect of the present invention there is provided promoter and upstream activating sequences usable for Aspergillus, especially *A. niger* expression and derived from an *A. niger* neutral α-amylase gene.

According to a second aspect of the present invention there is provided promoter and upstream activating sequences derived from an *A. niger* acid stable α-amylase gene.

According to a third aspect of the present invention there is provided promoter and upstream activating sequences derived from a previously undescribed amylase from *A. niger* (*A. niger* XA amylase).

The neutral and acid stable α-amylases from *A. niger* are described by Minoda et al., Agr. Biol. Chem. 33 (4), 572–578 (1969).

According to a fourth aspect of the present invention there is provided a process for expression of a protein product in Aspergillus comprising the steps of:

(a) providing a recombinant DNA cloning vector system capable of integration into the genome of an Aspergillus host in one or more copies and comprising: promoter and upstream activating sequences derived from an *A. niger* amylase gene; a suitable marker for selection of transformants; and a DNA-sequence encoding the desired protein product;

(b) transforming the Aspergillus host which does not harbour a functional gene for the chosen selection marker with the recombinant DNA cloning vector system from step a; and (c) culturing the transformed Aspergillus host in a suitable culture medium.

The host strain is preferably an *Aspergillus niger* strain although other Aspergillus strains may be used.

According to a fifth aspect of the present invention there is provided a method for production of a protein product in *Aspergillus niger* by which method an *Aspergillus niger* strain being transformed with a recombinant DNA cloning vector system as described above is cultured in a suitable culture medium and the product is recovered from the culture medium.

According to a sixth aspect of the present invention there is provided a previously undescribed amylase from *A. niger*.

BRIEF DESCRIPTION OF THE DRAWINGS:

The present invention is further illustrated by reference to the accompanying drawings in which:

FIG. 1 shows an endonuclease restriction map of plasmids pNA1 and pNA2,

FIG. 2 shows the DNA-sequence of the *A. niger* neutral α-amylase promoter NA1 and upstream activating regions, the preregion and the 5' part of the structural gene for the *A. niger* neutral α-amylase, FIG. 3 shows the DNA-sequence of the *A. niger* neutral α-amylase promoter NA2 and upstream activating sequences, the preregion and the 5' part of the structural gene for the A. niger neutral α-amylase.

FIG. 5 shows the DNA-sequence of the XA niger amylase promoter and upstream activating sequences together with the preregion and the 5' part of the structural gene.

DETAILED DESCRIPTION OF THE INVENTION

Figure 4:
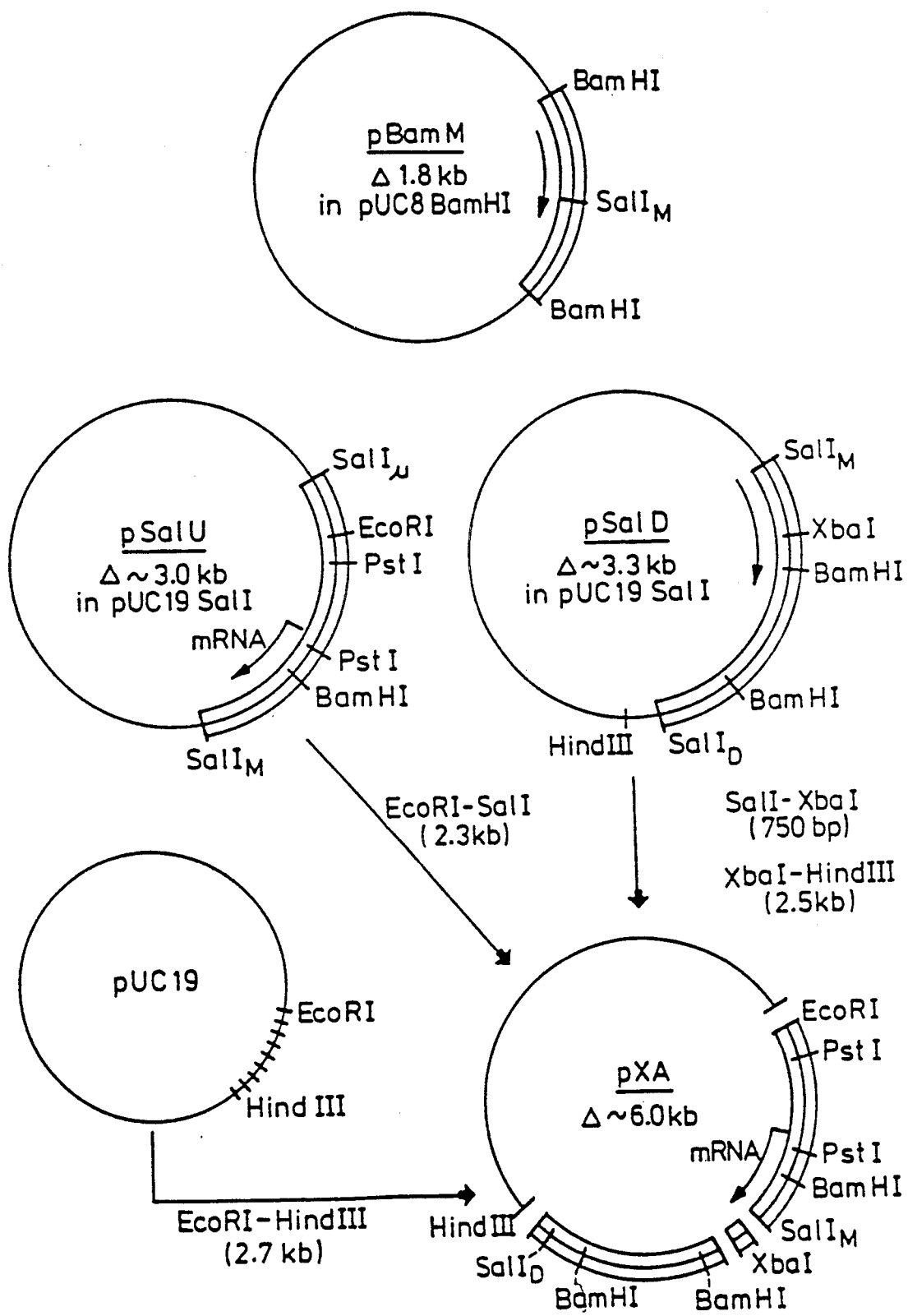
FIG. 4 shows the construction of plasmid pXA.

The transformation technique used was a method adapted from the methods for transformation of *A. nidulans* (Ballance et al. Biochem. Biophys. Res. Commun., 112 (1983), 284–289; Tilburn et al., Gene 26 (1983), 205–221, Yelton et al. Proc. Natl. Acad. Sci. U.S.A., 81 (1984), 1470–1474) and similar to the method of Buxton et al. (Gene 37 (1985), 207–214) for transformation of *A. niger*. In the process of the present invention the chosen Aspergillus strain is transformed with a vector system containing a selection marker which is capable of being incorporated into the genome of the host strain, but which is not harboured in the host strain before the transformation. Transformants can then be selected and isolated from nontransformants on the basis of the incorporated selection marker.

Preferred selection markers are the argB (*A. nidulans* or *A. niger*), trpC (*A. nidulans*), amdS (*A. nidulans*), or pyr4 (*Neurospora crassa*) genes, or the DHFR (dihydrofolate reductase or mutants hereof) gene. More preferred selection markers are the argB or the amdS gene.

Besides promoter and upstream activating sequences the vectors will normally contain further DNA-sequences encoding functions facilitating gene expression such as transcription terminators and polyadenylation signals.

As described in further detail in example 1 DNA-sequences encoding the *A. niger* neutral α-amylase including the preregion and promoter and upstream activating sequences were derived from a *A. niger* mycelium and inserted into HindIII digested pUC8 to give plasmids pNA1 and pNA2 (see FIG. 1). In pNA1 the *A. niger* derived DNA is shown as a 8.0 kb HindIII-HindIII fragment. The established DNA-sequence of the promoter and upstream activating sequences is shown in FIG. 2. The promoter ends at nucleotide-1 preceding the Met(1) codon of the neutral α-amylase presequence. The nucleotide sequence encoding the presequence is constituted of 63 nucleotides and the mature α-amylase starts at a position corresponding to nucleotide 64. In pNA2 the *A. niger* derived DNA is shown as a 4.0 kb HindIII-HindIII fragment. The established DNA-sequence of the promoter and upstream activating sequences is shown in FIG. 3. The promoter ends at nucleotide-1 preceding the Met(1) codon of the α-amylase presequence. The nucleotide sequence encoding the presequence is constituted of 63 nucleotides and the mature neutral α-amylase starts at a position corresponding to nucleotide 64.

From pNA1 and pNA2 the whole promoter sequence including sequences upstream to the promoter or functional parts thereof may be derived by means evident to the person skilled in the art. The promoter sequence may be provided with linkers with the purpose of introducing specific restriction sites facilitating the ligation of the promoter sequence with further DNA, for instance the gene encoding the desired protein product or different preregions (signal peptides).

According to one embodiment of the present invention the NA1 promoter and upstream activating sequences have the following sequence or a functionally equivalent nucleotide sequence:

| | | | | |
|---|---|---|---|---|
| TCTAAACGTC | GTCAAAGGTC | TGTCTTCTTT | CCGTATTGTC | ATCTTGTAAT |
| ACGCTTCCTC | AATGTCGTAT | TTCGAAAAGA | AACGGGCTTT | CTTTATCCAA |
| TCCCTGTGGT | AAGATTGATC | GTCAGGAGAT | TATCTGCAGG | AAACATCATG |
| GTGGGGTAAC | CAAGGTTGTG | TCTGTATAAT | ATATACATGT | AAAATACATG |
| AGCTTCGGTG | ATATAATACA | GAAGTACCAT | ACAGTACCGC | GTTATGAAAA |
| CACATTAATC | CGGATCCTTT | CCTATAATAG | ACTAGCGTGC | TTGGCATTAG |
| GGTTCGAAAA | ACAATCGAAG | AGTATAAGGG | GATGACAGCA | GTAACGACTC |
| CAACTGTACG | CCTCCGGGTA | GTAGTCCGGA | CAGCCGAGCC | AGCTCAGCGC |
| CTAAAACGCC | TTATACAATT | AAGCAGTTAA | AGAAGTTAGA | ATCTACGCTT |
| AAAAAGCTAC | TTAAAAATCG | ATCTCGCAGT | CCCGATTCGC | CTATCAAAAC |
| CAGTTTAAAT | CAACTGATTA | AAGGTGCCGA | ACGAGCTATA | AATGATATAA |
| CAATATTAAA | GCATTAATTA | GAGCAATATC | AGGCCGCGCA | CGAAAGGCAA |
| CTTAAAAGCG | AAAGCGCTCT | ACTAAACAGA | TTACTTTTGA | AAAAGGCACA |
| TCAGTATTTA | AAGCCCGAAT | CCTTATTAAG | CGCCGAAATC | AGGCAGATAA |
| AGCCATACAG | GCAGATAGAC | CTCTACCTAT | TAAATCGGCT | TCTAGGCGCG |
| CTCCATCTAA | ATGTTCTGGC | TGTGGTGTAC | AGGGGCATAA | AATTACGCAC |
| TACCCGAATC | GATAGAACTA | CTCATTTTTA | TATAGAAGTC | AGAATTCATG |
| GTGTTTTGAT | CATTTTAAAT | TTTTATATGG | CGGGTGGTGG | GCAACTCGCT |
| TGCGCGGCAA | CTCGCTTACC | GATTACGTTA | GGGCTGATAT | TTACGTAAAA |
| ATCGTCAAGG | GATGCAAGAC | CAAAGTAGTA | AAACCCCGGA | GTCAACAGCA |
| TCCAAGCCCA | AGTCCTTCAC | GGAGAAACCC | CAGCGTCCAC | ATCACGAGCG |
| AAGGACCACC | TCTAGGCATC | GGACGCACCA | TCCAATTAGA | AGCAGCAAAG |
| CGAAACAGCC | CAAGAAAAAG | GTCGGCCCGT | CGGCCTTTTC | TGCAACGCTG |
| ATCACGGGCA | GCGATCCAAC | CAACACCCTC | CAGAGTGACT | AGGGGCGGAA |
| ATTTAAAGGG | ATTAATTTCC | ACTCAACCAC | AAATCACAGT | CGTCCCCGGT |
| ATTGTCCTGC | AGAATGCAAT | TTAAACTCTT | CTGCGAATCG | CTTGGATTCC |
| CCGCCCCTAG | CGTAGAGCTT | AAAGTATGTC | CCTTGTCGAT | GCGATGTATC |
| ACAACATATA | AATACTAGCA | AGGGATGCCA | TGCTTGGAGG | ATAGCAACCG |
| ACAACATCAC | ATCAAGCTCT | CCCTTCTCTG | AACAATAAAC | CCCACAGAAG |

GCATTT representing the sequence from nucleotide −1456 to −1 in FIG. 2.

According to a further embodiment the NA2 promoter and upstream activating sequences have the following sequence or a functionally equivalent nucleotide sequence:

| | | | | |
|---|---|---|---|---|
| AAGCTTCCAG | CTACCGTAGA | TTACTGATAC | AAACTCAATA | CACTATTTCT |
| ATAACCTTAC | TGTTCAATAC | AGTACGATCA | AAATTTCCGG | AATATTAATG |
| TTACGGTTAC | CTTCCATATG | TAGACTAGCG | CACTTGGCAT | TAGGGTTCGA |
| AATACGATCA | AAGAGTATTG | GGGGGGGTGA | CAGCAGTAAT | GACTCCAACT |
| GTAAATCGGC | TTCTAGGCGC | GCTCCATCTA | AATGTTCTGG | CTGTGGTGTA |
| CAGGGGCATA | AAATTACGCA | CTACCCGAAT | CGATAGAACT | ACTCATTTTT |
| ATATAGAAGT | CAGAATTCAT | GGTGTTTTGA | TCATTTTAAA | TTTTTATATG |
| GCGGGTGGTG | GGCAACTCGC | TTGCGCGGCA | ACTCGCTTAC | CGATTACGTT |
| AGGGCTGATA | TTTACGTAAA | AATCGTCAAG | GGATGCAAGA | CCAAAGTACT |
| AAAACCCCGG | AGTCAACAGC | ATCCAAGCCC | AAGTCCTTCA | CGGAGAAACC |
| CCAGCGTCCA | CATCACGAGC | GAAGGACCAC | CTCTAGGCAT | CGGACGCACC |
| ATCCAATTAG | AAGCAGCAAA | GCGAAACAGC | CCAAGAAAAA | GGTCGGCCCG |
| TCGGCCTTTT | CTGCAACGCT | GATCACGGGC | AGCGATCCAA | CCAACACCCT |
| CCAGAGTGAC | TAGGGGCGGA | AATTTATCCG | GATTAATTTC | CACTCAACCA |
| CAAATCACAG | TCGTCCCCGG | TATTGTCCTG | CAGAATGCAA | TTTAAACTCT |
| TCTGCGAATC | GCTTGGATTC | CCCGCCCCTA | GCGTAGAGCT | TAAAGTATGT |
| CCCTTGTCGA | TGCGATGTAT | CACAACATAT | AAATACTAGC | AAGGGATGCC |
| ATGCTTGGAG | GATAGCAACC | GACAACATCA | CATCAAGCTC | TCCCTTCTCT |
| GAACAATAAA | CCCCACAGAA | GGCATTT representing the sequence | | | from nucleotide −927 to −1 in FIG. 3.

When comparing the NA1-sequence with the NA2-sequence it appears that they have almost identical sequences in part of the upstream activating region. These sequences extend up to nucleotide −725 and further from nucleotide −1129 to −1099 in FIG. 2 and from nucleotide −755 to −725 in FIG. 3.

According to a still further embodiment of the present invention the *A. niger* XA derived promoter and upstream activating sequences have the following nucleotide sequence

| | | | | |
|---|---|---|---|---|
| CCTAATGACC | CAACATTGGC | TGCGGTTGAG | ACTCAATTCA | TGGTTGGGCC |
| GGCCATCATG | GTGGTCCCGG | TATTGGAGCC | TCTGGTCAAT | ACGGTCAAGG |
| GCGTATTCCC | AGGAGTTGGA | CATGGCGAAG | TGTGGTACGA | TTGGTACACC |
| CAGGCTGCAG | TTGATGCGAA | GCCCGGGGTC | AACACGACCA | TTTCGGCACC |
| ATTGGGCCAC | ATCCCAGTTT | ATGTACGAGG | TGGAAACATC | TTGCCGATGC |
| AAGAGCCGGC | ATTGACCACT | CGTGAAGCCC | GGCAAACCCC | GTGGGCTTTG |
| CTAGCTGCAC | TAGGAAGCAA | TGGAACCGCG | TCGGGGCAGC | TCTATCTCGA |
| TGATGGAGAG | AGCATCTACC | CCAATGCCAC | CCTCCATGTG | GACTTCACGG |
| CATCGCGGTC | AAGCCTGCGC | TCGTCGGCTC | AAGGAAGATG | GAAAGAGAGG |
| AACCCGCTTG | CTAATGTGAC | GGTGCTCGGA | GTGAACAAGG | TGCCCTCTGC |
| GGTGACCCTG | AATGGACAGG | CCGTATTTCC | CGGGTCTGTC | ACGTACAATT |
| CTACGTCCCA | GGTTCTCTTT | GTTGGGGGGC | TGCAAAACTT | GACGAAGGGC |
| GGCGCATGGG | CGGAAAACTG | GGTATTGGAA | TGGTAGTGTC | AGCCACAAGC |
| CAGGTGTGCG | CGTACAGCAT | GCAACATGGG | AACGATGCTC | TGCAATGTAG |
| CTCTTTGGTT | ATAATTCAAA | ATTCAACTTC | CACCTTTGTT | TCACCGGCGG |
| CCACGGCATT | CCTGCATGAC | TAACGTTCTG | TAAATGGACC | CGATAACACC |
| CAGCACGTTG | CAGCAGAGAA | GGTACTCTCT | CACACGCACT | GCTCTTTATA |
| GTTGCCGAGA | CGGCCGCCGA | GGAGAAAACC | GCCGGCCTGT | GGCCACTATT |
| CGCTGGAAGG | AACCCTGCCA | GTCGAACACA | CCCGCCCGTG | ATCGCCAGGG |
| GCCGATGGAT | TTCCCCCCGC | ATCCTTGTCG | GTTCATGAGT | GAAGACTTTA |
| AATCCATCT | AGCTGACGGT | CGGGTACATC | AATAACTGGC | GGCCTGGTTT |
| CCAGGACACG | GAGAGGCATC | TAATCGCTAT | TTATAGAATG | CTGGGATCGG |
| ACCCGTCGAA | TGGTCTTCCG | ATGGGAAGTG | ACAACTCACA | TTGTCATGTT |
| GGCCTTACTC | AATCCAACGG | GATCTGACCT | GCTTTGGCTA | ACCTAGTATA |
| AATCAGCATG | TCTCTCCTTT | GATACATCGG | ATCGTTCCTC | AAATATAGTT |
| ATATCTTCGA | AAAATTGACA | AGAAGG | | | or a functionally equivalent sequence. This sequence represents the sequence from nucleotide −1 to −1276 in FIG. 5.

Figure 6:
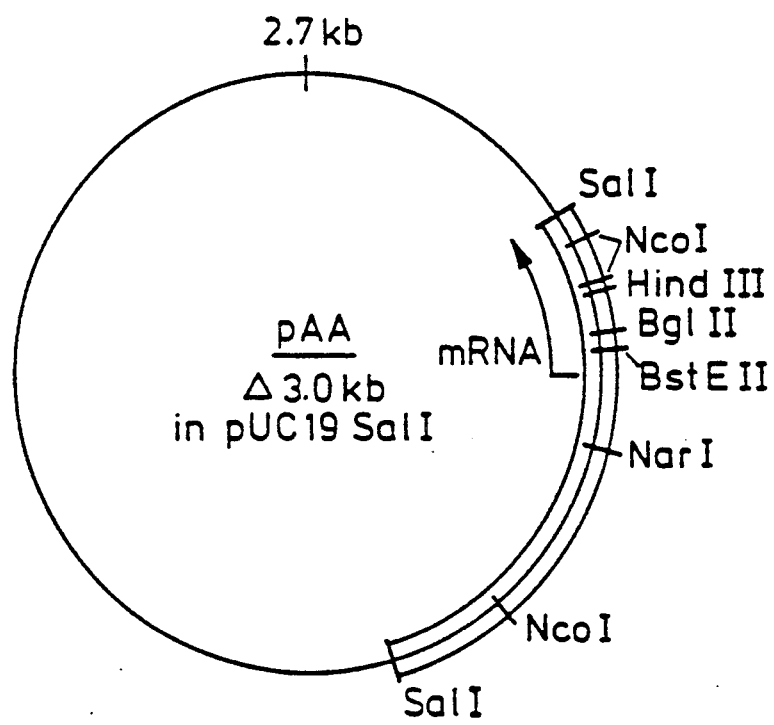
FIG. 6 shows plasmid pAA, FIG. 7a and b show the DNA-sequence of the acid-stable α-amylase promoter and upstream activating sequences together with the preregion and the 5' part of the structural gene.

The *A. niger* acid stable α-amylase promoter may be derived from plasmid pAA (FIG. 6 and example 3). The promoter and upstream activating sequences are included in the SalI-BstEII fragment of pAA. The DNA-sequence of the promoter including upstream activating sequences together with the 5' part of the mature acid-stable α-amylase gene is shown in FIG. 7a and b.

The present invention is contemplated to include use of the above indicated sequences or functional parts or fragments thereof.

The terminators and polyadenylation sequences may be derived from the same sources as the promoters. Enhancer sequences may also be inserted into the construction.

The expressed product may be accumulated within the cells requiring disruption of the cells to isolate the product. To avoid this further process step and also to minimize the amount of possible degradation of the expressed product within the cells it is preferred that the product is secreted from the cells. For this purpose the gene for the desired product is provided with a preregion ensuring effective direction of the expressed product into the secretory pathway of the cell. This preregion which might be a naturally occurring signal or leader peptide or functional parts thereof or a synthetic sequence providing secretion is generally cleaved from the desired product during secretion leaving the mature product ready for isolation from the culture broth.

The preregion may be derived from genes for secreted proteins from any source of organism.

According to the present invention the preregion may be derived from a glucoamylase or an amylase gene from an Aspergillus species, an amylase gene from a Bacillus species, a lipase or proteinase gene from *Rhizomucor miehei*, the gene for the α-factor from *S. cerevisiae*, the calf prochymosin gene or from the gene for the protein product to be produced by the transformed strain. More preferably the preregion is derived from the gene for *A. oryzae* TAKA amylase, *A. niger* neutral α-amylase, *A. niger* acid-stable α-amylase, preregion from XA amylase, *B. licheniformis* α-amylase, the maltogenic amylase from Bacillus NCIB 11837, *B. stearothermophilus* α-amylase or *B. licheniformis* subtilisin.

The TAKA-amylase signal and the *A. niger* neutral α-amylase signal have the following sequence ATGATGGTCGCGTGGTGGTCTCTATTTCTGTACGGCCTTCAGGTCGCGGCACCTGCTTTGGCT
Met Met Val Ala Trp Trp Ser Leu Phe Leu Tyr Gly Leu Gln Val Ala Ala Pro Ala Leu Ala The gene for the desired product functionally linked to the promoter and terminator sequences may be incorporated in a vector containing the selection marker or may be placed on a separate vector or plasmid capable of being integrated into the genome of the host strain. As used herein the expression "vector system" includes a single vector or plasmid or two or more vectors or plasmids which together contain the total DNA-information to be integrated into the host genome. Vectors or plasmids may be linear or closed circular molecules. According to a preferred embodiment of the present invention *A. niger* is cotransformed with two vectors, one including the selection marker and the other comprising the remaining foreign DNA to be introduced in the host strain, including promoter, the gene for the desired product and transcription terminator and polyadenylation sequences.

Normally the *A. niger* transformants are stable and can be cultured in the absence of a selection pressure. If the transformants turn out to be unstable the selection marker may be used for selection during cultivation. The transformed cells are then cultured under a selection pressure corresponding to the marker in question.

The present invention provides for a method for production of high yields of many different polypeptide or protein products in Aspergillus, especially *A. niger*. *A. niger* strains have for years been used in commercial scale for the production of for instance amyloglucosidase and other extracellular enzymes and accordingly fermentation technology for these microorganisms is well developed and the microorganisms are approved for use in the food industry. The present invention offers the possibility of using *A. niger* in the industrial production of high amounts of in principle any polypeptide or protein product. Examples of such products are chymosin or prochymosin and other rennets, proteases, amyloglucosidases, acid stable amylases from Aspergillus, fungal lipases or prokaryotic lipases, and thermostable bacterial and fungal amylases.

The genes for these enzymes were obtained from cDNA libraries or genomic libraries as described in further detail in the following.

The present invention is also directed to a novel amylase from *A. niger*. The cloning of the gene for this previously undescribed amylase is described in the following example 2. From the DNA-sequence for the gene for the mature amylase (XA) the following amino acid sequence was deduced for the novel amylase:

Ala—Thr—Pro—Ala—Glu—Trp—Arg—Ser—Gln—Ser—Ile—Tyr—Phe—Leu—
Leu—Thr—Asp—Arg—Phe—Ala—Arg—Thr—Asp—Asn—Ser—Thr—Thr—Ala—
Ser—Cys—Asp—Leu—Ser—Ala—Arg—Gln—Tyr—Cys—Gly—Gly—Ser—Trp—
Gln—Gly—Ile—Ile—Asn—Gln—Leu—Asp—Tyr—Ile—Gln—Gly—Met—Gly—
Phe—Thr—Ala—Ile—Trp—Ile—Thr—Pro—Val—Thr—Ala—Gln—Ile—Pro—
Gln—Asp—Thr—Gly—Tyr—Gly—Gln—Ala—Tyr—His—Gly—Tyr—Trp—Gln—
Gln—Asp—Ala—Tyr—Ala—Leu—Asn—Ser—His—Tyr—Gly—Thr—Ala—Asp—
Asp—Leu—Lys—Ala—Leu—Ala—Ser—Ala—Leu—His—Ser—Arg—Gly—Met—
Tyr—Leu—Met—Val—Asp—Val—Val—Ala—Asn—His—Met—Gly—His—Asn—
Gly—Thr—Gly—Ser—Ser—Val—Asp—Tyr—Ser—Val—Tyr—Arg—Pro—Phe—
Asn—Ser—Gln—Lys—Tyr—Phe—His—Asn—Leu—Cys—Trp—Ile—Ser—Asp—
Tyr—Asn—Asn—Gln—Thr—Asn—Val—Glu—Asp—Cys—Trp—Leu—Gly—Asp—
Asn—Thr—Val—Ala—Leu—Pro—Asp—Leu—Asp—Thr—Thr—Ser—Thr—Glu—
Val—Lys—Asn—Met—Trp—Tyr—Asp—Trp—Val—Glu—Ser—Leu—Val—Ser—
Asn—Tyr—Ser—Val—Asp—Gly—Leu—Arg—Val—Asp—Thr—Val—Lys—Asn—
Val—Gln—Lys—Asn—Phe—Trp—Pro—Gly—Tyr—Asn—Asn—Ala—Ser—Gly—
Val—Tyr—Cys—Ile—Gly—Glu—Val—Phe—Asp—Gly—Asp—Ala—Ser—Tyr—
Thr—Cys—Pro—Tyr—Gln—Glu—Asp—Leu—Asp—Gly—Val—Leu—Asn—Tyr—
Pro—Met—Tyr—Tyr—Pro—Leu—Leu—Arg—Ala—Phe—Glu—Ser—Thr—Asn—
Gly—Ser—Ile—Ser—Asp—Leu—Tyr—Asn—Met—Ile—Asn—Tyr—Val—Lys—
Ser—Thr—Cys—Arg—Asp—Ser—Thr—Leu—Leu—Gly—Thr—Phe—Val—Glu—
Asn—His—Asp—Asn—Pro—Arg—Phe—Ala—Lys—Tyr—Thr—Ser—Asp—Met—
Ser—Leu—Ala—Lys—Asn—Ala—Ala—Thr—Phe—Thr—Ile—Leu—Ala—Asp—.
Gly—Ile—Pro—Ile—Ile—Tyr—Ala—Gly—Gln—Glu—Gln—His—Tyr—Ser—
Gly—Gly—Asn—Asp—Pro—Tyr—Asn—Arg—Glu—Ala—Thr—Trp—Leu—Ser—
Gly—Tyr—Lys—Thr—Thr—Ser—Glu—Leu—Tyr—Thr—His—Ile—Ala—Ala—
Ser—Asn—Lys—Ile—Arg—Thr—His—Ala—Ile—Lys—Gln—Asp—Thr—Gly—
Tyr—Leu—Thr—Tyr—Lys—Asn—Tyr—Pro—Ile—Tyr—Gln—Asp—Thr—Ser—
Thr—Leu—Ala—Met—Arg—Lys—Gly—Tyr—Asn—Gly—Thr—Gln—Thr—Ile—
Thr—Val—Leu—Ser—Asn—Leu—Gly—Ala—Ser—Gly—Ser—Ser—Tyr—Thr—
Leu—Ser—Leu—Pro—Gly—Thr—Gly—Tyr—Thr—Ala—Gly—Gln—Lys—Ile—
Thr—Glu—Ile—Tyr—Thr—Cys—Thr—Asn—Leu—Thr—Val—Asn—Ser—Asn—
Gly—Ser—Val—Pro—Val—Pro—Met—Lys—Ser—Gly—Leu—Pro—Arg—Ile—
Leu—Tyr—Pro—Ala—Asp—Lys—Leu—Val—Asn—Gly—Ser—Ser—Phe—Cys—
Ser

The above amino acid sequence shows 74% homology to the TAKA-amylase enzyme.

The present invention is contemplated to include an amylase enzyme with the above amino acid sequence or a sequence closely related thereto as long as variations

EXAMPLE 1

Cloning of the *A. niger* neutral α-amylase genes

Mycelium from *A. niger* DSM 2761 was harvested and processed for preparation of DNA according to the method described by Boel et al., EMBO Journal 3, 1581-85 (1984). The chromosomal DNA was cut with BamHI, EcoRI, SalI, and HindIII and analyzed by Southern blotting essentially according to Southern, J. Mol. Biol. 98, 503-18 (1975). A partial cDNA clone for TAKA-amylase was used as hybridization probe covering the first 300 amino acids of the structural gene. The TAKA-amylase cDNA clone was prepared as described in published EP patent application No. 0238023. The choice of probe is based on the similarity between TAKA-amylase from *A. oryzae* and the neutral α-amylase from *A. niger* (Minoda et al., Agr. Biol. Chem. 33 (4), 572-78 (1969)). The Southern analysis shows that *A. niger* has 2 genes for neutral α-amylase. For cloning we chose HindIII digestion where the 2 genes are represented by fragments of about 8.0 kb and 4.0 kb, respectively which were inserted into HindIII digested, dephosphorylated pUC8 (Vieira et al., Gene 19, 259-68 (1982)). From 5000 clones of each kind we found 1 HindIII clone of 8.0 kb and 4 HindIII clones of 4.0 kb, which hybridized with TAKA-amylase cDNA. Restriction maps of the plasmids pNA1 and pNA2 carrying the two amylase genes are shown in FIG. 1. Both plasmids contain full length amylase genes with promoters and upstream activating sequences.

EXAMPLE 2

Cloning of the gene coding for a so far undescribed amylase in *A. niger*

On the Southern blot described in example 1 the neutral α-amylase genes hybridized strongly to the TAKA-amylase cDNA probe. On the same blot the cDNA probe was seen to hybridize weakly to other genes, which would indicate a structural relationship to the amylase. Thus, on the basis of weak hybridization we cloned from *A. niger* DSM 2761 a 1.8 kb BamHI fragment into BamHI digested, dephosphorylated pUC8 and from SalI digestion we cloned fragments of 3.0-3.5 kb into SalI digested, dephosphorylated pUC19 (Messing, Meth. in Enzymology 101, 20-27 (1983)). There were two kinds of SalI clones which turned out to cover about half of the structural gene each. The clones covering the N-terminal have about 2.0 kb upstream of the signal sequence. The BamHI clones were found to cover parts of both types of SalI clones with the connecting SalI site almost in the middle. FIG. 4 shows the three plasmids, pBamM, pSalU and pSalD and the constructed plasmid pXA with the complete gene including promoter and upstream activating sequences. Analysis of the amino acid sequence shows 74% homology to TAKA-amylase which should leave no doubt that the cloned gene is indeed coding for an amylase. The designation for it will be XA.

The DNA-sequence of the XA-amylase promoter and upstream activating sequences, the preregion and the 5' part of the structural gene is shown in FIG. 5.

EXAMPLE 3

Cloning of the *A. niger* acid α-amylase gene

The Southern blot described in example 1 was hybridized to an oligonucleotide probe

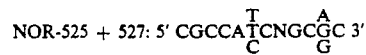

covering the N-terminal amino acids 3-7 in the acid stable α-amylase. One of the hybridizing fragments was a SalI fragment of about 3.0 kb which was cloned into SalI digested, dephosphorylated pUC19. From 20,000 clones 10 were found which hybridized to NOR-525+527. They all had the same 3.0 kb SalI insert as shown in FIG. 6. Sequence analysis shows that about half of the structural gene for the acid stable α-amylase is present while promoter and upstream sequences cover about 2.0 kb.

EXAMPLE 4

Expression of *A. niger* neutral α-amylase in *A. oryzae*

*A. oryzae* was used as host to analyze the potential of the *A. niger* neutral α-amylase promoters, as the gene product is much more stable in *A. oryzae* than in *A. niger*. Also, it is assumed that the promoters perform at least as well in their inherent host *A. niger* as in *A. oryzae*.

*A. oryzae* IFO 4177 was transformed with pNA1 and pNA2 respectively, using selection on acetamide by cotransformation with p3SR2 harbouring the amdS gene from *A. nidulans* (Tilburn, J. G. et al., Gene 26, 205-221 (1913)). Transformation was performed as described in the published EP patent application No. 0238023.

The two types of transformants were grown at 30° C. in YPD medium (Sherman et al., Methods in Yeast Genetics, Cold Spring Harbor Laboratory (1981)). After 3-6 days of growth, culture supernatants were analyzed by SDS-PAGE, followed by Coomassie stain or ELISA on Western blot. The expression level of neutral α-amylase from both types of transformants was up to 10 times higher than in the untransformed IFO 4177 harbouring its own neutral α-amylase, called TAKA-amylase. In the transformants the yield of amylase was about 1 g/l supernatant thus demonstration the efficiency of the promoter and upstream activating sequences from these two genes.

EXAMPLE 5

Expression vectors containing promoter and upstream activating sequences from *A. niger* amylase genes followed by the prepro-sequence of Rhizomucor miehei aspartic protease Aspartic protease from *Rhizomucor miehei* (in the following called RMP) is chosen to demonstrate the production and secretion of a heterologous protein in *A. niger* and *A. oryzae* using upstream sequences from *A. niger* amylase genes to promote synthesis.

The 3 constructions to be outlined below have some common features. One is the use of pRMP AMG Term, the plasmid donating the RMP gene. This plasmid is described in detail in the published EP patent application No. 0238023. It has a BamHI site 9 bp upstream of the ATG initiating the preregion and following the structural gene of RMP it has a terminator sequence from the *A. niger* glucoamylase gene. Another feature is the use of exonuclease III→S1 nuclase→Klenow fragment, according to Henikoff, S. Gene 28, 351–59 (1984) in order to cut back (100–200 bp) from a site downstream of the initiating ATG in the amylase genes to obtain a blunt end just upstream of the ATG and thus be able to pick up a BamHI site (from pUC 19) to join to the BamHI site in pRMP AMG Term.

Figure 8:
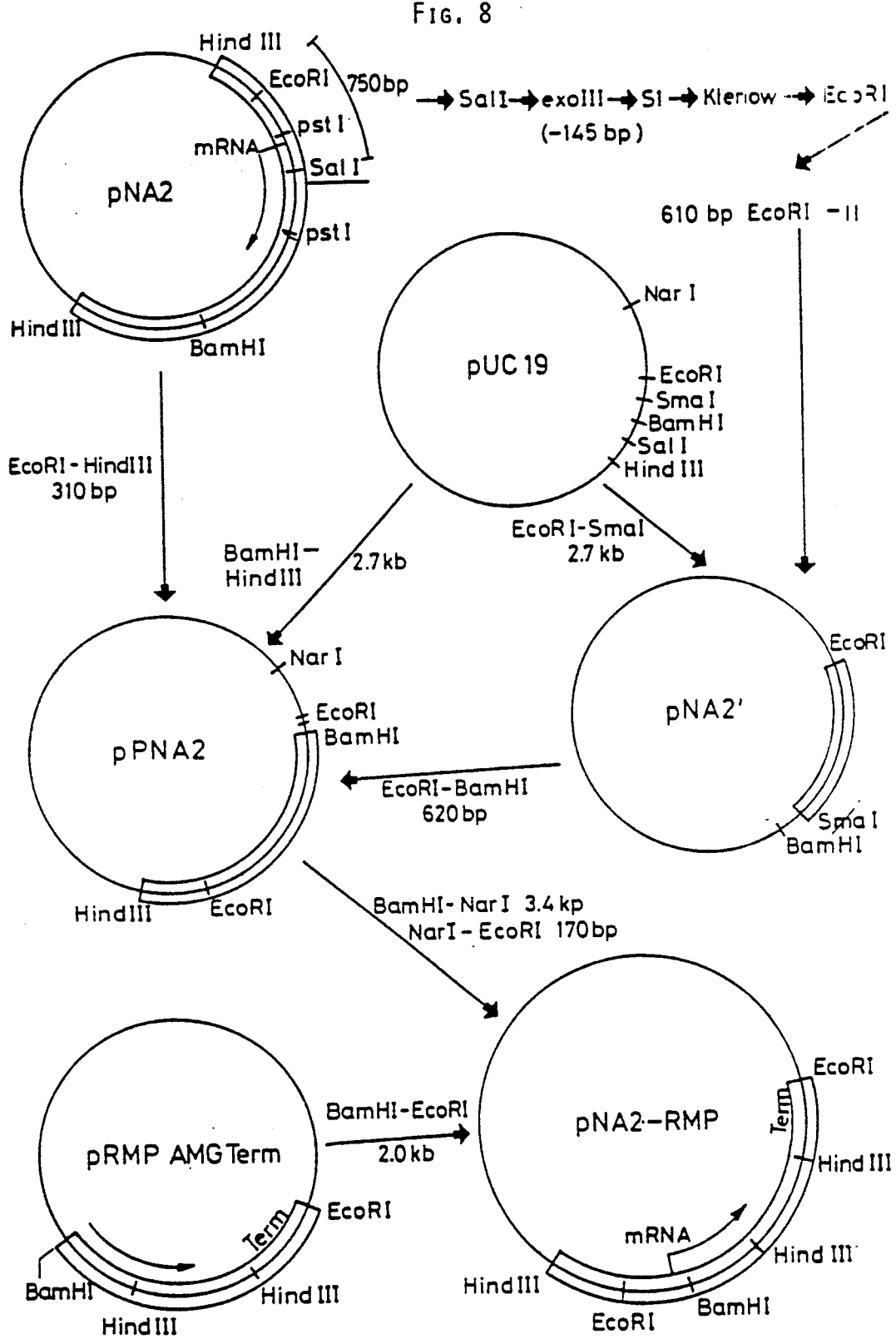
FIG. 8 shows the construction of plasmid pNA2-RMP.

FIG. 8 illustrates the construction of the RMP gene under control of the promoter and upstream activating sequences from the neutral α-amylase gene in pNA2 (FIG. 1). Approximately 145 bp are cut back from SalI site, as verified by sequencing later, to yield an EcoRI-blunt end fragment of about 610 bp. This fragment is inserted into pUC19 cut with SmaI and EcoRI and cut out again as a 620 bp EcoRI-BamHI fragment. This fragment is ligated to a 310 bp EcoRI-HindIII fragment from upstream pNA2 and pUC19 cut with BamHI and HindIII to yield pPNA2. From this plasmid a BamHI-NarI fragment of 3.4 kb and a NarI-EcoRI fragment of 170 bp are ligated to a BamHI-EcoRI 2.0 kb from pRMP AMG Term to give the expression vector pPNA2-RMP.

Figure 9:
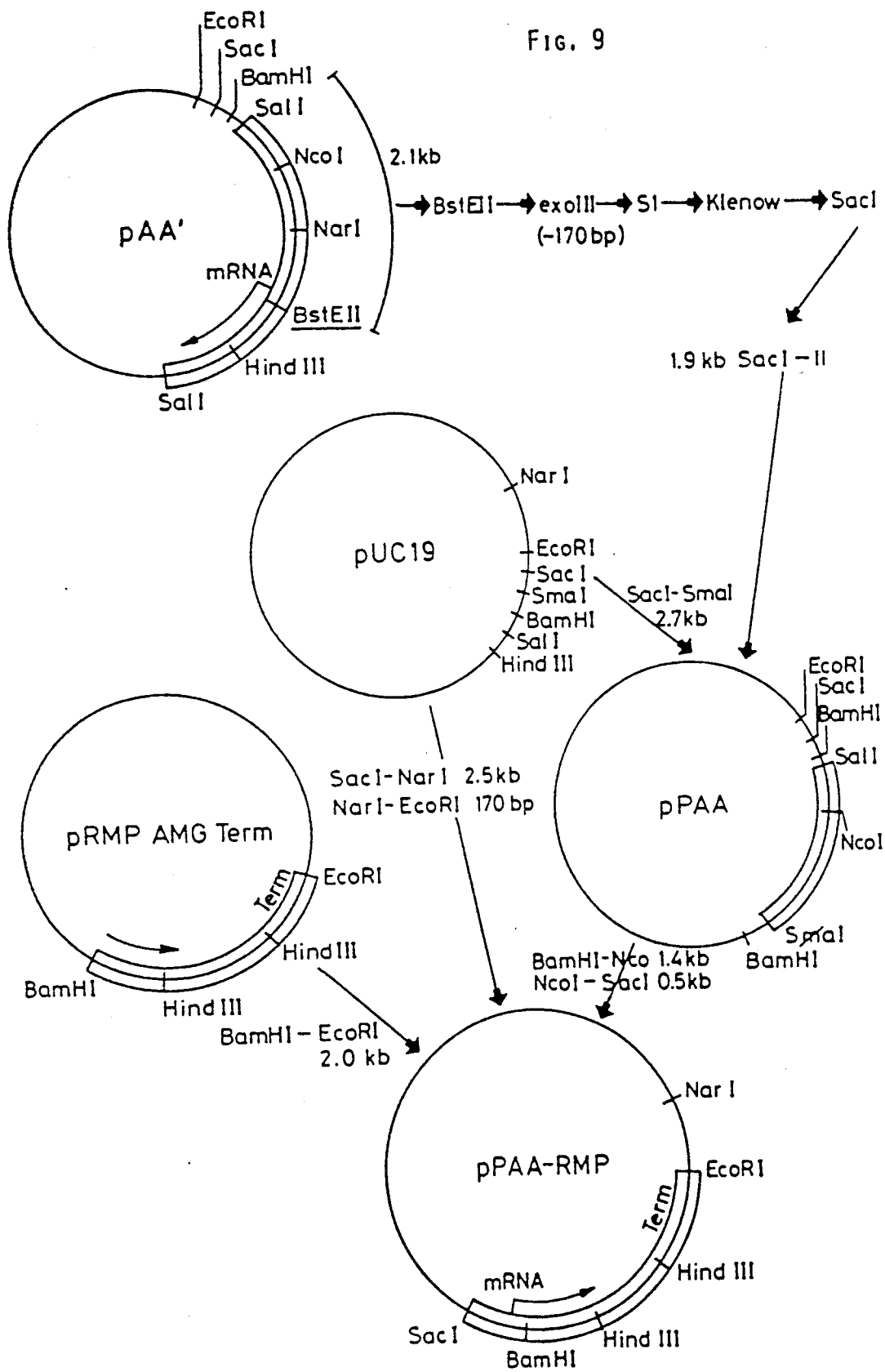
FIG. 9 shows the construction of plasmid pPAA-RMP and FIG. 10 shows the construction of plasmids pPXA-RMP and pPXA-RMP'

FIG. 9 shows the construction of the RMP gene under control of the promoter and upstream activating sequences from the acid amylase gene in pAA′, where the gene is inserted in pUC19 in the opposite orientation of pAA (FIG. 6). About 170 bp are cut back from BstEII site to yield a fragment of 1.9 kb when cut with SacI. This SacI-blunt end fragment is inserted into pUC19 cut with SmaI and SacI and excised again as two fragments BamHI-NcoI 1.4 kb and NcoI-SacI 0.5 kb. These fragments are ligated to fragment BamHI-EcoRI 2.0 kb from pRMP AMG Term and two fragments from pUC19, SacI-NarI 2.5 kb and NarI-EcoRI 170 bp, to give the expression plasmid pPAA-RMP.

Figure 10:
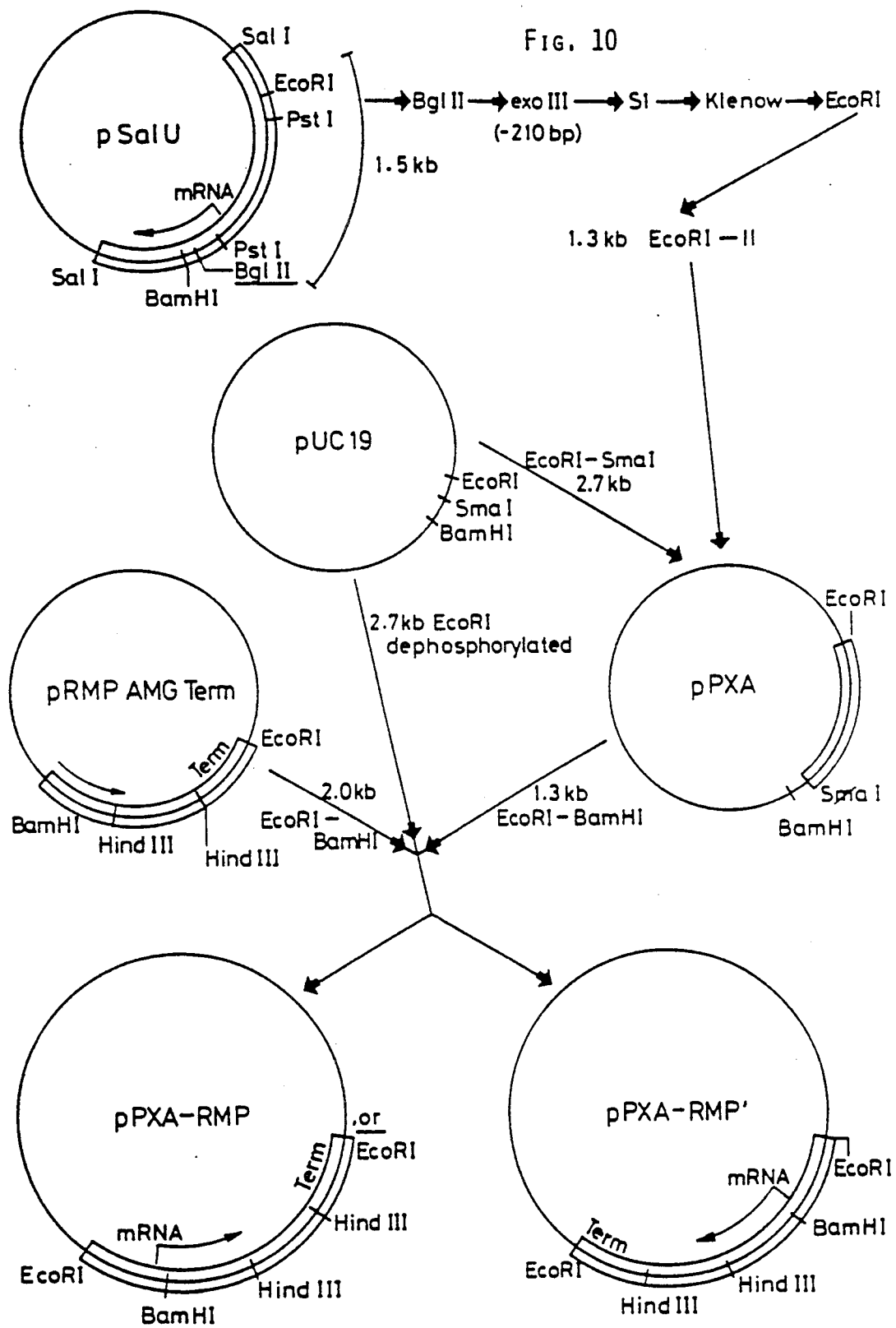

FIG. 10 outlines the construction of the RMP gene under control of the promoter and upstream activating sequences from the new amylase gene in pSalU (FIG. 4). About 210 bp are cut off from the BglII site to yield a fragment of 1.3 kb when cut with EcoRI. This fragment is inserted into pUC19 EcoRI-SmaI 2.7 kb to pick up the BamHI site next to the blunt end. The final ligation of 2.0 kb EcoRI-BamHI from pRMP AMG Term, 1.3 kb EcoIR-BamHI from pPXA and pUC19 2.7 kb EcoRI dephosphorylated fragment yields two correct expression plasmids pPXA-RMP and pPXA-RMP′ with the gene in either orientation. The incorrect plasmids having 2 EcoRI-BamHI fragments of the same kind are easily discriminated by restriction analysis.

The expression plasmids are transformed into *A. niger* (Kelly, J. M. and Hynes, M. J., EMBO Journal 4, 475–479 (1985) and Buxton, F. P., et al., Gene 37, 207–214 (1985) using argB as selection marker and into *A. oryzae* as outlined above. Transformants grown in YPD are analyzed on SDS-PAGE as above and activity of the protease RMP is measured.

I claim:

1. A promoter and upstream activating sequence derived from an *Aspergillus niger* neutral alpha-amylase gene having the following sequence.

```
TCTAAACGTC  GTCAAGGTC   TGTCTTCTTT
            CCGTATTGTC  ATCTTGTAAT

ACGCTTCCTC  AATGTCGTAT  TTCGAAAAGA
            AACGGGCTTT  CTTTATCCAA

TCCCTGTGGT  AAGATTGATC  GTCAGGAGAT
            TATCTGCAGG  AAACATCATG

GTGGGGTAAC  CAAGGTTGTG  TCTGTATAAT
            ATATACATGT  AAAATACATG

AGCTTCGGTG  ATATAATACA  GAAGTACCAT
            ACAGTACCGC  GTTATGAAAA

CACATTAATC  CGGATCCTTT  CCTATAATAG
            ACTAGCGTGC  TTGGCATTAG

GGTTCGAAAA  ACAATCGAAG  AGTATAAGGG
            GATGACAGCA  GTAACGACTC

CAACTGTACG  CCTCCGGGTA  GTAGTCCGAG
            CAGCCGAGCC  AGCTCAGCGC

CTAAAACGCC  TTATACAATT  AAGCAGTTAA
            AGAAGTTAGA  ATCTACGCTT

AAAAAGCTAC  TTAAAAATCG  ATCTCGCAGT
            CCCGATTCGC  CTATCAAAAC

CAGTTTAAAT  CAACTGATTA  AAGGTGCCGA
            ACGAGCTATA  AATGATATAA

CAATATTAAA  GCATTAATTA  AAGGTGCCGA
            ACGAGCTATA  AATGATATAA

CAATATTAAA  GCATTAATTA  GAGCAATATC
            AGGCCGCGCA  CGAAAGGCAA

CTTAAAAGCG  AAAGCGCTCT  ACTAAACAGA
            TTACTTTTGA  AAAAGGCACA

TCAGTATTTA  AAGCCCGAAT  CCTTATTAAG
            CGCCGAAATC  AGGCAGATAA

AGCCATACAG  GCAGATAGAC  CTCTACCTAT
            TAAATCGGCT  TCTAGGCGCG

CTCCATCTAA  ATGTTCTGGC  TGTGGTGTAC
            AGGGGCATAA  AATTACGCAC

TACCCGAATC  GATAGAACTA  CTCATTTTTA
            TATAGAAGTC  AGAATTCATG

GTGTTTTGAT  CATTTTAAAT  TTTTATATGG
            CGGGTGGTGG  GCAACTCGCT

TGCGCGGCAA  CTCGCTTACC  GATTACGTTA
            GGGCTGATAT  TTACGTAAAA

ATCGTCAAGG  GATGCAAGAC  CAAAGTAGTA
            AAACCCCGGA  GTCAACAGCA

TCCAAGCCCA  AGTCCTTCAC  GGAGAAACCC
            CAGCGTCCAC  ATCACGAGCG

AAGGACCACC  TCTAGGCATC  GGACGCACCA
            TCCAATTAGA  AGCAGCAAAG

CGAAACAGCC  CAAGAAAAAG  GTCGGCCCGT
            CGGCCTTTTC  TGCAACGCTG

ATCACGGGCA  GCGATCCAAC  CAACACCCTC
            CAGAGTGACT  AGGGGCGGAA

ATTTAAAGGG  ATTAATTTCC  ACTCAACCAC
            AAATCACAGT  CGTCCCCGGT

ATTGTCCTGC  AGAATGCAAT  TTAAACTCTT
            CTGCGAATCG  CTTGGATTCC

CCGCCCCTAG  CGTAGAGCTT  AAAGTATGTC
            CCTTGTCGAT  GCGATGTATC

ACAACATATA  AATACTAGCA  AGGGATGCCA
            TGCTTGGAGG  ATAGCAACCG

ACAACATCAC  ATCAAGCTCT  CCCTTCTCTG
            AACAATAAAC  CCCACAGAAG
```

-continued

GCATTT derived from an *Aspergillus niger* neutral alpha-amylase gene having the following sequence

| AAGCTTCCAG | CTACCGTAGA | TTACTGATAC | AAACTCAATA | CACTATTTCT |
| ATAACCTTAC | TGTTCAATAC | AGTACGATCA | AAATTTCCGG | AATATTAATG |
| TTACGGTTAC | CTTCCATATG | TAGACTAGCG | CACTTGGCAT | TAGGGTTCGA |
| AATACGATCA | AAGAGTATTG | GGGGGGGTGA | CAGCAGTAAT | GACTCCAACT |
| GTAAATCGGC | TTCTAGGCGC | GCTCCATCTA | AATGTTCTGG | CTGTGGTGTA |
| CAGGGGCATA | AAATTACGCA | CTACCCGAAT | CGATAGAACT | ACTCATTTTT |
| ATATAGAAGT | CAGAATTCAT | GGTGTTTTGA | TCATTTTAAA | TTTTTATATG |
| GCGGGTGGTG | GGCAACTCGC | TTGCGCGGCA | ACTCGCTTAC | CGATTACGTT |
| AGGGCTGATA | TTTACGTAAA | AATCGTCAAG | GGATGCAAGA | CCAAAGTACT |
| AAAACCCCGG | AGTCAACAGC | ATCCAAGCCC | AAGTCCTTCA | CGGAGAAACC |
| CCAGCGTCCA | CATCACGAGC | GAAGGACCAC | CTCTAGGCAT | CGGACGCAAA |
| ATCCAATTAG | AAGCAGCAAA | GCGAAACAGC | CCAAGAAAAA | GGTCGGCCCG |
| TCGGCCTTTT | CTGCAACGCT | GATCACGGGC | AGCGATCCAA | CCAACACCCT |
| CCAGAGTGAC | TAGGGGCGGA | AATTTATCGG | GATTAATTTC | CACTCAACCA |
| CAAATCACAG | TCGTCCCCGG | TATTGTCCTG | CAGAATGCAA | TTTAAACTCT |
| TCTGCGAATC | GCTTGGATTC | CCCGCCCCTA | GCGTAGAGCT | TAAAGTATGT |
| CCCTTGTCGA | TGCGATGTAT | CACAACATAT | AAATACTAGC | AAGGGATGCC |
| ATGCTTGGAG | GATAGCAACC | GACAACATCA | CATCAAGCTC | TCCCTTCTCT |
| GAACAATAAA | CCCCACAGAA | GGCATTT | | | or a fragment thereof having substantially the same promoter activity as said sequence.

2. A promoter and upstream activating sequence or a fragment thereof having substantially the same promoter activity as said sequence.

* * * * *